United States Patent [19]

Sioshansi et al.

[11] Patent Number: 5,474,797
[45] Date of Patent: Dec. 12, 1995

[54] BACTERICIDAL COATINGS FOR IMPLANTS

[75] Inventors: Piran Sioshansi, Lincoln; Eric J. Tobin, Burlington; John E. Barry, Everett; Robert S. Farivar, Chestnut Hill, all of Mass.

[73] Assignee: Spire Corporation, Bedford, Mass.

[21] Appl. No.: 195,822

[22] Filed: Feb. 10, 1994

Related U.S. Application Data

[63] Continuation of Ser. No. 780,275, Oct. 18, 1991, abandoned.

[51] Int. Cl.[6] .................... B05D 1/04; A61L 2/14; A61L 2/20; A61L 27/00
[52] U.S. Cl. .................. 427/2.24; 427/2.28; 427/2.30; 427/525; 427/531
[58] Field of Search .................. 427/2.12, 2.24, 427/2.28, 525, 528, 531, 2.3

[56] References Cited

U.S. PATENT DOCUMENTS

| | | | |
|---|---|---|---|
| 3,557,795 | 1/1971 | Hirsch | 128/335.5 |
| 3,589,975 | 6/1971 | Andrews et al. | 161/165 |
| 3,695,921 | 10/1972 | Shepherd et al. | 117/72 |
| 3,699,956 | 10/1972 | Kitrilakis et al. | 128/348 |
| 4,027,393 | 1/1977 | Ellis . | |
| 4,039,699 | 8/1977 | Morimoto et al. | 427/38 |
| 4,054,139 | 10/1977 | Crossley | 604/265 |
| 4,152,478 | 5/1979 | Takagi | 428/221 |
| 4,253,463 | 3/1981 | Kim | 128/348 |
| 4,281,029 | 7/1981 | Takagi et al. | 427/38 |
| 4,374,717 | 2/1983 | Drauglis et al. | 204/192 C |
| 4,388,164 | 6/1983 | Kolev et al. | 204/192 SP |
| 4,411,648 | 10/1983 | Davis et al. | 604/21 |
| 4,440,108 | 4/1984 | Little et al. | 118/719 |
| 4,443,488 | 4/1984 | Little et al. | 427/38 |
| 4,452,827 | 6/1984 | Kolev et al. | 427/38 |
| 4,476,590 | 10/1984 | Scales et al. | 606/76 |
| 4,479,795 | 10/1984 | Mustacich et al. | 604/53 |

(List continued on next page.)

FOREIGN PATENT DOCUMENTS

| | | |
|---|---|---|
| 0029787 | 6/1981 | European Pat. Off. .................. 606/76 |
| 206-024-A | 12/1986 | European Pat. Off. . |
| 87307136 | 3/1988 | European Pat. Off. . |
| 3228-849-A | 2/1984 | Germany . |
| 3302-567-A | 7/1984 | Germany . |
| 3830359 | 12/1989 | Germany .................. 623/11 |
| PCT/CA91/ 00453 | 7/1992 | WIPO . |
| PCT/US92/ 08266 | 4/1993 | WIPO . |
| PCT/US93/ 00685 | 8/1993 | WIPO . |
| PCT/CA93/ 00201 | 11/1993 | WIPO . |

OTHER PUBLICATIONS

Dennis G. Maki; M.D. et al. "Infection Control in Intravenous Therapy," *Annals of Internal Medicine* 79:867–887; 1973.

John L. Tully, M. D. et al. "Complications of Intravenous Therapy with Steel Needles and TEFLON® Catheters–A Comparative Study", vol. 70, Mar. 1981, 702–706 *Amer. Journ. of Med.*

(List continued on next page.)

Primary Examiner—Diana Dudash
Attorney, Agent, or Firm—Thomas J. Engellenner; John V. Bianco; Lahive & Cockfield

[57] ABSTRACT

Polymeric implants provided with coatings of bactericidal compounds in the form of ionized atoms by a vapor process. The polymeric implants include products designed to penetrate or enter the body, such as catheters, shunts connectors and the like. Coatings of bactericidal compounds on the polymeric implants are intended to make their use safe. The coatings are formed thereon in the form of ionized atoms of the compounds by ion-beam-assisted deposition in a vacuum chamber. The vacuum chamber is provided, inter alia, with an evaporator and an ion source mounted in operative association therein, including means for rotatably mounting a plurality of polymeric implants for exposure to the evaporator and the ion source.

8 Claims, 6 Drawing Sheets

U.S. PATENT DOCUMENTS

| | | | |
|---|---|---|---|
| 4,581,028 | 4/1986 | Fox, Jr. et al. | 623/2 |
| 4,592,920 | 6/1986 | Murtfeldt | 427/2 |
| 4,683,149 | 7/1987 | Suzuki et al. | 427/38 |
| 4,693,760 | 9/1987 | Sioshansi | 148/4 |
| 4,718,905 | 1/1988 | Freeman | 623/6 |
| 4,743,308 | 5/1988 | Sioshansi et al. | 148/4 |
| 4,743,493 | 5/1988 | Sioshansi et al. | 428/217 |
| 4,846,834 | 7/1989 | von Recum et al. | 623/11 |
| 4,855,026 | 8/1989 | Sioshansi | 204/192.11 |
| 4,871,366 | 10/1989 | von Recum et al. | 623/11 |
| 4,872,922 | 10/1989 | Bunker et al. | 148/4 |
| 4,886,505 | 12/1989 | Haynes et al. | 604/265 |
| 4,923,450 | 5/1990 | Maeda et al. | 604/265 |
| 4,936,281 | 6/1990 | Stasz | 606/48 |
| 4,994,060 | 2/1991 | Rink et al. | 606/7 |
| 5,049,140 | 9/1991 | Brenner et al. | 604/265 |
| 5,057,106 | 10/1991 | Kasevich et al. | 606/33 |
| 5,067,491 | 11/1991 | Taylor, II et al. | 128/673 |
| 5,069,227 | 12/1991 | Maronian et al. | 165/173 |
| 5,165,952 | 11/1992 | Solomon et al. | 427/2 |
| 5,223,309 | 6/1993 | Farivar | 427/525 |
| 5,236,509 | 8/1993 | Sioshansi et al. | 119/719 |
| 5,308,704 | 5/1994 | Suzuki et al. | 427/525 |

OTHER PUBLICATIONS

Gerald Friedland, M. D. "Infusion–Related Phlebitis–Is the In–Line Filter the Solution?" *The New England Journal of Medicine,* vol. 312 No. 2, Jan. 10, 1985, 113–115.

Kenneth H. Falchuk, M.D. et al. "Microparticulate–Induced Phlebitis," *The New England Journal of Medicine,* vol. 312, No. 2, Jan. 10, 1985, 78–82.

J. Lewis et al "Assessment of Thromboresistance of Intravenous Cannulae by $^{125}$I–Fibrinogen Scanning", *Journ. of Biomed. Mat. Res.,* vol. 19, 99–113 (1985).

John Power M. D. et al. "Fatal Bacterial Endocarditis as a Complication of Permanent Indwelling Catheters" *Amer. Journ. of Med.* vol. 81 pp. 166–168 Jul. 1986.

T. S. J. Elliott "Intravascular–Device Infections" *J. Med. Microbid* vol. 27 (1988) pp. 161–167.

H. Liedberg et al "Assessment of Silver–coated Urinary Catheter Toxicity by Cell Culture" *Urol. Res.* (1989) 17:359–360.

H. Liedberg et al. "Silver Alloy Coated Catheters Reduce Catheter–Associated Bacteriuria" *British Journal of Urology* (1990) 65, 379–381.

P. Bentivegna M.D. et al. "The Vitacull and Intravascular Catheter–Related Infection" *JAMA* Aug. 4, 1989 No. 262, vol. 5 pp. 613–614.

M. Corona M. D. et al. "Infections Related to Central Venous Catheters" *Mayo Clinic Proc.* Jul. 1990 vol. 65, pp. 979–986.

B. M. Farr, M. D. "Vascular Catheter–Related Infectious" *Current Opinion in Infectious Diseases* 1990 3:513–516.

J. Johnson et al. "Prevention of Catheter Associated Urinary Tract Infection with a Silver Oxide–Coated Urinary Catheter: Clinical and Microbiologic Correlates" *Journal of Infectious Diseases* 1990; 162:1145–1150.

Chaim Putterman "Central Venous Catheter Relates Sepsis: A Clinical Review" *Resuscitation,* 20(1990) 1–16.

P. Kumar et al. "Wear Resistent Properties of Various Prosthetic Joint Materials" *Adv. in Biomaterials* vol. 9 (1990) pp. 373–378.

Murphy et al "The Small Pin Circular Fixator for Proximal Tibial Fractures with Soft Tissue Comprise" *Orthopedics* Mar. 1991 vol. 14 No. 3, pp. 273–280.

Mahan et al. "Factors In Pin Tract Infections" *Orthopedics* Mar. 1991 vol. 14 No. 3, pp. 305–308.

Solnick–Legg et al. (Apr. 1989) "Ion Beam and Plasma Technology for Improved Biocompatible Surfaces", MRS BULLETIN, pp. 27–30.

Haywood "Dual IBAD Makes Good Coatings", *Advanced Materials and Processes,* vol. 138, Issue 6, publication of The Materials Information Society, Dec. , 1990.

IBAT Brochure, Spire Corporation, Bedford, Mass., published Mar. 8, 1991.

SPI–ARGENT™ Brochure, published Oct. 9, 1992.

SPI–ARGENT™ Technical Brochure, published Apr. 23, 1993.

BACTERICIDAL COATINGS FOR IMPLANTS

This application is a file wrapper continuation of U.S. patent application Ser. No. 07/780,275, filed Oct. 18, 1991 now abandoned.

BACKGROUND OF THE INVENTION

1. Field of the Invention

The present invention relates generally to implants and, more particularly, to implants provided with bactericidal coatings so as not only to improve their antimicrobial properties, but also to make the implants fight germinating bacteria in situ.

2. The Prior Art

In a related co-pending application Ser. No. 07/663,361, filed Mar. 1, 1991, now abandoned, of Mohammed Farivar and Piran Sioshansi, entitled "Metallized Polymeric Implants, Methods and Apparatus," and assigned to a common assignee, Spire Corporation, Bedford, Mass., there are disclosed and claimed surface metallized polymeric implants, a method and an apparatus to improve the implants' biocompatibility and to reduce infusion-associated phlebitis and infection, twin commendable goals pulling in opposing direction. The disclosure of said application Ser. No. 07/663,361 is incorporated herein by reference.

For, efforts directed at fighting infection, the overriding consideration of this invention, does of necessity reduce biocompatibility. The balancing of these two goals is a delicate test facing the medical practitioner.

In applications where the implant is intended for relatively short dwell time within the body, in particular in the use of external fixation devices to immobilize a broken limb while it heals, infection-fighting ability of the device becomes paramount at the expense of biocompatibility. This is what is addressed by this invention.

Infections, such as nosocomial infections (infections originating in a hospital), result from polymeric, metallic and/or ceramic implanted devices, including external fixation devices, indwelling urological catheters and the like, being placed in the body. Medical device manufacturers have not employed bacteriostatic compounds as antimicrobial agents in such indwelling devices because of the difficulties associated with producing an adherent, long lasting film on such polymeric, metallic and/or ceramic surfaces. It has been noted that using ion-beam-assisted deposition technique (IBAD), well-adhering, ductile thin films of bacteriostatic/fungistatic compounds also can be applied to biomedical products.

The common assignee herein, Spire Corporation of Bedford, Mass., has been one of the pioneers in the field of ion beam technology. A plasma-supported ion beam technique for coating industrial cutting tools with a thin layer of cubic boron nitride to improve the tools' cutting properties is disclosed in U.S. Pat. No. 4,440,108, of Roger G. Little et al, granted Apr. 3, 1984, and assigned to said Spire Corporation. A plasma-ion deposition process of large-grain, thin semiconductor films directly on low-cost amorphous substrates is disclosed in U.S. Pat. No. 4,443,488, also of Roger G. Little et al, granted Apr. 17, 1984 and assigned to said Spire Corporation. A process of preventing surface discoloration in titanium orthopaedic implants by ion implantation is disclosed in U.S. Pat. No. 4,693,760 of Piran Sioshansi granted Sep. 15, 1987 and assigned to said Spire Corporation. An ion implantation process for plastics to enhance their surface hardness and their resistance to chemical attack is disclosed in U.S. Pat. No. 4,743,493 of Piran Sioshansi et al, granted May 10, 1988 and assigned to said Spire Corporation. A process for passivating the electrochemically active surface of metal alloys so as to inhibit their corrosion is disclosed in U.S. Pat. No. 4,743,308 of Piran Sioshansi et al, granted May 10, 1988 and assigned to said Spire Corporation. A sputter-enhanced ion implantation process, primarily of ball bearings, without the use of a separate evaporation system is disclosed in U.S. Pat. No. 4,855,026 of Piran Sioshansi, granted Aug. 8, 1989 and assigned to said Spire Corporation. An improved method and apparatus for the uniform ion implantation of spherical surfaces, such as ball bearings, is disclosed in U.S. Pat. No. 4,872,922 of Stephen N. Bunker et al, granted Oct. 10, 1989 and assigned to said Spire Corporation. A method of depositing an ionized cluster on a substrate is disclosed in U.S. Pat. No. 4,152,478 of Toshinori Takagi, granted May 1, 1979. And a method of coating a substrate with a stoichiometric compound is disclosed in U.S. Pat. No. 4,281,029 of Toshinori Takagi et al, granted Jul. 28, 1981. The use of ion beam processing is thus well known and widespread.

SUMMARY OF THE INVENTION

It is a principal object of the present invention to overcome the above disadvantages by providing polymeric, metallic and ceramic implants with well adhering thin films of bactericidal compounds so as to render them infection fighting during their indwell time.

More specifically, it is an object of the present invention to provide polymeric, metallic and ceramic implants with thin films of bactericidal compounds, such as external fixation devices, skeletal fixation pins, catheters of all sorts, stents, laryngectomy flaps, tracheostomy tubes, hydrocephalic shunts, percutaneous connectors, hemodialysis ports, voice prosthesis, wound drainage devices, dental implants, closed looped ventilation tubes, ceramic and metallic counterfaces in joint replacements and the like.

The biomedical implant essentially comprises an implant of the above-enumerated group, a coating of bactericidal compound enveloping the same, with the bactericidal compound being formed as one or more of the following: platinum, iridium, gold, silver, mercury, copper, iodine, alloys, compounds and oxides thereof, the bactericidal coating being formed thereon in the form of ionized atoms of the compound within a vacuum chamber by beam-assisted deposition (IBAD), with the chamber including an ion source and an evaporator.

Other objects of the present invention will in part be obvious and will in part appear hereinafter.

The invention accordingly comprises the polymeric, metallic and/or ceramic implants provided with coatings of bactericidal compounds of the present disclosure, its components, parts and their interrelationships, the scope of which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein.

DETAILED DESCRIPTION OF THE PREFERRED EMBODIMENTS

Figure 1:
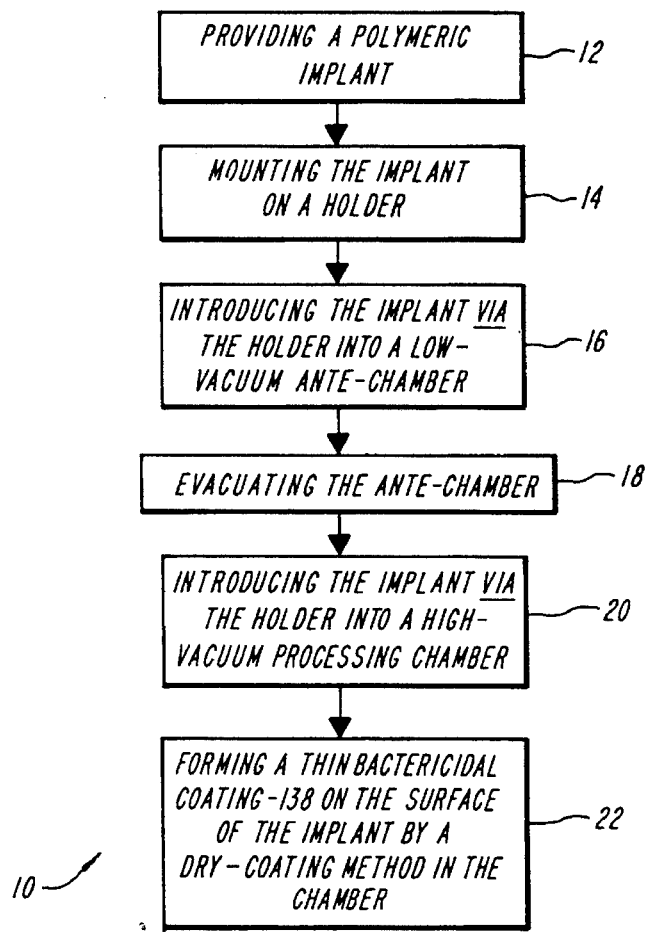
FIG. 1 is a flow diagram of a preferred process of applying the bactericidal compound coating to an implant.

In said co-pending application Ser. No. 07/663,361, entitled "Metallized Polymeric Implants, Method and Apparatus", and assigned to said common assignee, Spire Corporation, Bedford, Mass., there have been disclosed and claimed surface metallized polymeric implants, a method and an apparatus designed to render such polymeric implants biocompatible by reducing their infusion associated phlebitis and infection, the disclosure of which has been incorporated herein by reference.

The present invention, in general, relates to polymeric metallic and/or ceramic implants provided with well-adhering coatings of bactericidal compounds. The bactericidal compound coatings are not only infection resistant, but provide the implants with effective bacteria fighting attributes during their use as external fixation devices, pins, catheters of all types, ceramic and metallic counterfaces in joint replacements, percutaneous, connectors and the like.

The coatings of bactericidal compounds are formed on the surface of the implants in the form of ionized atoms of the compounds. Although the process of forming these bactericidal coatings is similar in application to that disclosed in said co-pending application Ser. No. 07/663,361, the herein preferred operational parameters are as follows: a vacuum pressure of about $10^{-7}$ torr, with the temperature of the implant during ion-beam-assisted deposition (IBAD) ranging from about $-76°$ C. to about $200°$ C., ion beam energy ranging from about 200 eV to about 20,000 eV, and a deposition rate on the surface of the implant being from about 10 to about 1,000 Angstroms per second. The preferred deposition thickness of the bactericidal coatings on the implants ranges from at least about 0.01 micron to about 2 microns.

Further, any ion beam apparatus capable of ion-beam assisted deposition can be used to provide the implants with the bactericidal coating compounds according to the invention. Such apparatus must have as a minimum, a vacuum chamber provided with an evaporator and an ion source.

The bactericidal compound is formed as one or more of the following: platinum, iridium, gold, silver, mercury, copper, iodine, and alloys, compounds and oxides thereof. In particular we have found that the ionized oxides of silver and gold do make for excellent bactericidal coatings and in addition, they also enhance the implants' physical appearance.

In an article recently published in the March 1991 issue of *Orthopedics*, Vol. 14, No. 3, "Factors in Pin Tract Infections," pp. 305–308, John Mahan, M.D. et al, state that in the use of skeletal external fixation devices (one being illustrated in FIG. 9 herein), the most significant complication is pin tract infection. The findings of these doctors show that, on examinations at the time of fixator removal, over 40% of the pin tracts were inflamed and about 75% of the pin tips cultured positive for bacteria. The predominant organism cultured was *Staphylococcus epidermidis* considered nonvirulent, followed by virulent *Staphylococcus aureus* and *Escherichia coli*. Their findings indicate that the bone-pin construct is not a sterile interface isolated from the environment. Rather it is a conduit between the surface of the skin, normally colonized by bacteria, and the medullary cavity, which is normally not. The bone-pin interface is subject to repetitive loading, which mechanical environment influences the bacterial colonization of the pin. The authors of the study hint at therapeutic manipulation of the bone-pin interface as a rational next step "in reducing the considerable complications attributed to infection of skeletal fixation pins." Id, at p. 308.

Applicants have come up with a better product which not only confers bacterial resistance to polymeric, metallic and/or ceramic medical implantable devices, but also provides such devices with a bactericidal coating which effectively fights bacteria itself, contributing thereby significantly to reducing pin tract infections.

Figure 2:
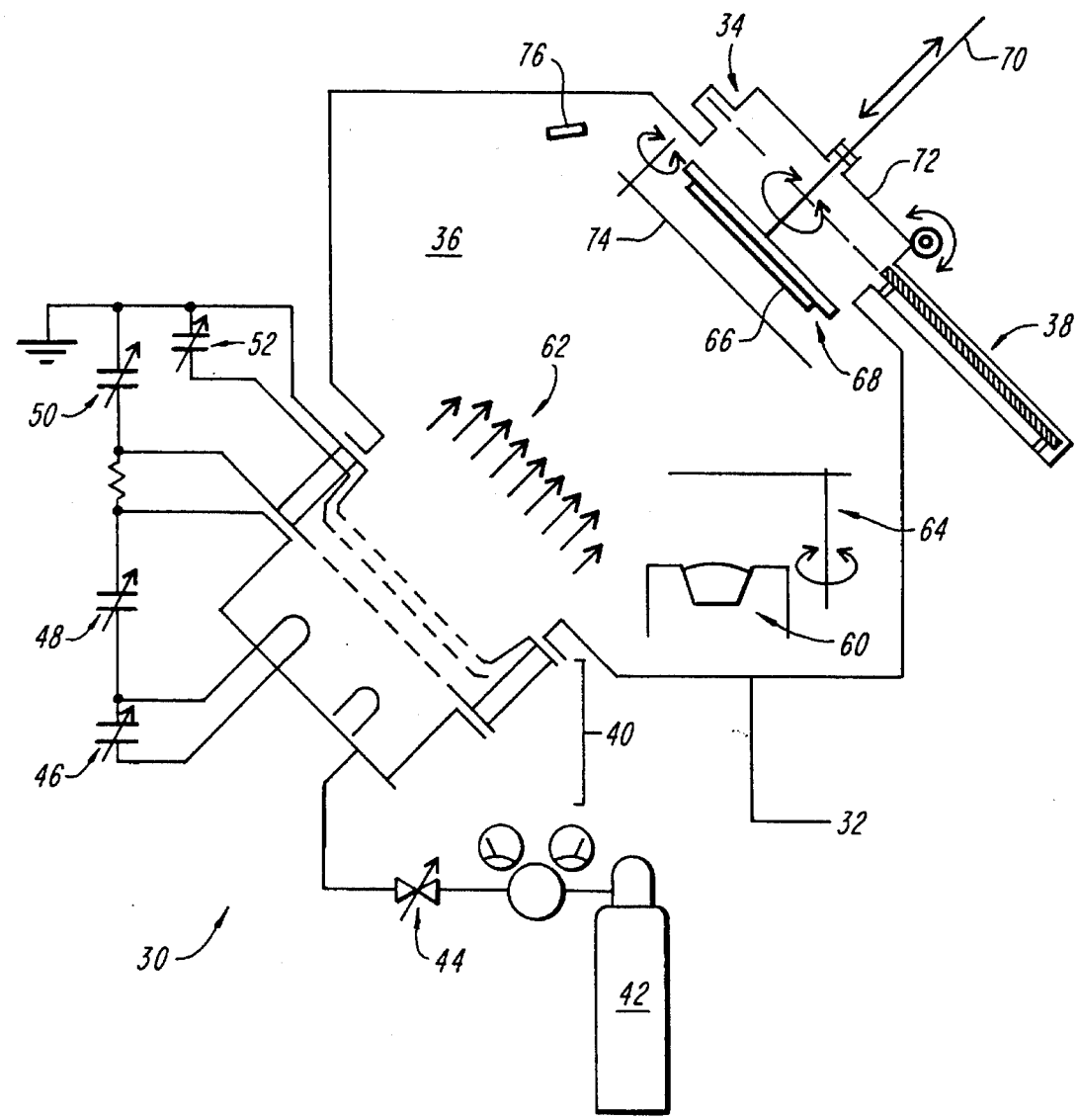
FIG. 2 is a schematic diagram of a preferred apparatus useful for applying the bactericidal compound coating to an implant.

THE EMBODIMENTS OF FIGS. 1 and 2

A flow diagram 10 of a preferred process of providing a bactericidal coating to polymeric, metallic and/or ceramic implants is illustrated in FIG. 1. The process essentially comprises the steps of providing 12 such an implant, mounting 14 the implant on a substrate holder, introducing 16 the implant via the substrate holder into a low-vacuum antechamber, evacuating 18 the low-vacuum antechamber to a high vacuum, further introducing 20 the implant via the substrate holder into a high-vacuum processing chamber, and forming 22 a thin coating of a bactericidal compound on the surface of the implant by a dry coating method within the high-vacuum processing chamber. Preferably, the dry coating method is an ion-beam process, such as an ion-beam-assisted deposition (IBAD) process. As known, ion beam processes are low-temperature, high-technology processes with excellent quality control to achieve good adherence, ductility, reproducibility, reliability and thickness of deposition control at a high throughput and with no chemical residues, thus being both environmentally and occupationally a safe, dependable technique.

A schematic diagram of a preferred apparatus 30 for practicing the above-described process is illustrated in FIG. 2. Apparatus 30 is designed to provide biomedical polymeric, metallic and/or ceramic implants with infection fighting coatings. The implants include external fixation devices, skeletal fixator pins, catheters of all sorts, stents, faryngectomy flaps, tracheostomy tubes, hydrocephalic shunts, percutaneous connectors, ceramic and metallic counterfaces in joint replacements and the like. Apparatus 30 essentially comprises a vacuum chamber system 32 formed of a low-vacuum antechamber 34 and a high vacuum processing chamber 36, air-tightly separated from each other by a gate 38 movable between a shown open position and a closed position shown in dashed lines.

An ion source 40, which can be a bucket type ion source, is mounted within the high-vacuum processing chamber 36 in a position diametrically opposed to the low-vacuum antechamber 34, substantially as shown. As known, the source 40 of ions is fed by one or more gases, such as argon, oxygen, neon and/or helium, from a suitable gas supply source 42, via a mass flow controller 44, regulating the rate of gas feed. A filament power supply 46 is provided to supply current to the filaments, an arc supply 48 to maintain an arc discharge between the anode and the filaments, an exit power supply 50 to accelerate the ions through the accelerator grid of the multiple grid system of the bucket type ion source 40, and a suppressor power supply 52 for negatively biasing the suppressor grid of the ion source 40 to reduce backstreaming of secondary electrons from the substrate.

An evaporator 60 also is mounted in the high-vacuum processor chamber 36 in operative association with the ion source 40. The evaporator 60 is designed to vaporize particular metallic evaporants so as to dry-coat a specific substrate therewith, being assisted in the dry-coating by an ion beam 62 emanating from the ion source 40. Metallic evaporants include mercury, copper, platinum, aluminum, nickel, iridium, silver, gold, and their respective alloys, oxides and compounds. A vapor shutter 64, designed to be rotated in and out of place of the evaporator 60, shields the substrates from the evaporants when in place. Substrates 66 to be dry-coated are introduced into the vacuum chamber system 32 of the dry-coating apparatus 30 with the aid of a suitable substrate holder 68. Preferably, the substrate holder 68 is mounted for both rotational and translatory motion on a shaft 70 and is introduced into the antechamber 34 through a hinge-like mounted end-plate 72. A pivotable shutter 74 is provided to shield the substrates 66 from the ion beam 62, when desired. A thickness monitor 76 preferably is provided in operative association with the substrate holder 68 to monitor the thickness of the thin metallic film being deposited on the substrate 68 during operation of the dry-coating apparatus 30.

The Embodiments of FIGS. 3–8

Figure 3:
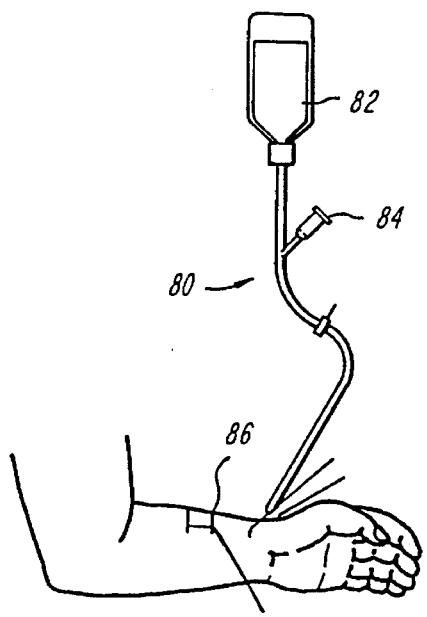
FIG. 3 is a schematic illustration of a typical intravenous infusion system in use.
Figure 4:
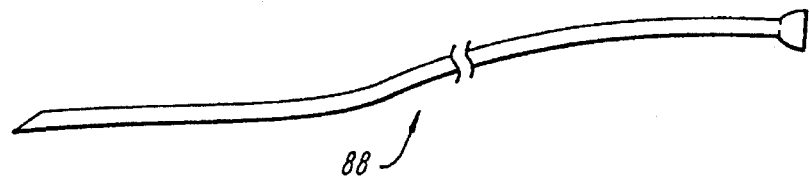
FIG. 4 illustrates a typical polymeric cannula for use in cardiovascular monitoring of a patient.
Figure 6:
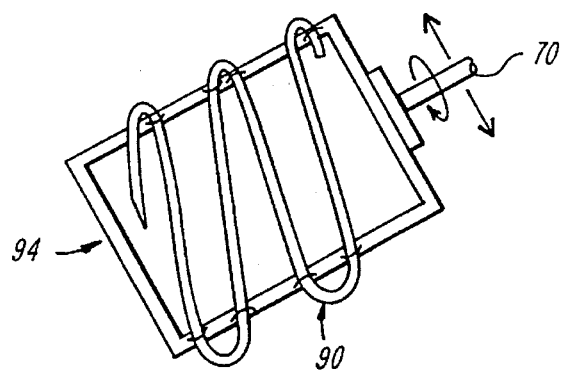
FIG. 6 is a view similar to FIG. 6 but illustrates the dry coating of a full length polymeric catheter.

In FIG. 3, a typical intravenous (I.V.) infusion system 80 is shown in operative use admitting a fluid 82 into an arm of a patient. If desired, other substances also can be added to the fluid 82 via a hypodermic needle 84 connected to the I.V. system 80. In this I.V. system 80, only the cannula 86 hereof is inserted into the vascular system of the patient. Hence only this cannula 86 portion of the system 80 need to be dry-coated with the thin bactericidal film. Other catheters 88 and 90, such as illustrated in FIGS. 4 and 6, are designed to be inserted substantially along their axial lengths, however, such as cardiac catheters and pulmonary artery catheters. Some of such catheters are formed with more than one lumen.

Figure 5:
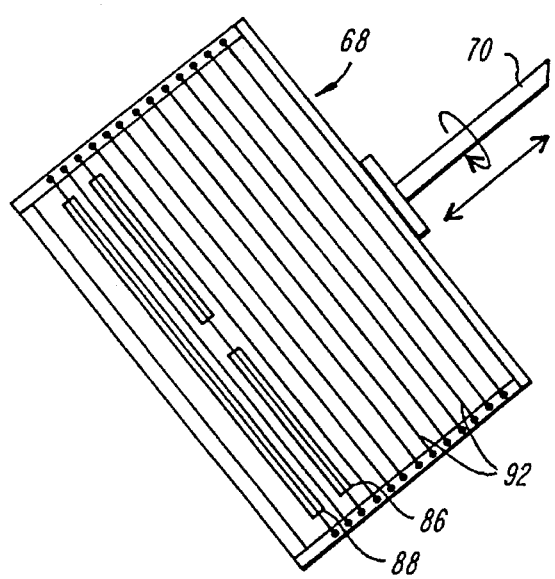
FIG. 5 is a schematic illustration of a modified part of the apparatus shown in FIG. 2, illustrating the dry coating of a plurality of polymeric catheters.

The dry-coating of polymeric catheter tips 86 and catheters 88 is illustrated in FIG. 5. As may be observed, the substrate holder 68 is formed as a cage, which is lengthwise adjustable and is lengthwise provided with a plurality of mandrils 92 to accommodate and securely hold a plurality of catheter tips 86 and catheters 88 respectively thereon. The substrate holder 68 preferably is rotated during the coating operation and is designed to be moved in translation between the antechamber 34 and the high-vacuum processing chamber 36 prior to the coating operation.

The dry-coating of the entire length of a rather long polymeric catheter 90 is illustrated in FIG. 6. A frame 94 is shown being mounted to the end of the shaft 70. Depending on the relative sizes of the catheter 90 versus the frame 94, one or more catheters 90 are loosely wound about the frame 94. Longer catheters or a number of catheters can be processed on larger frames 94.

Figure 7:
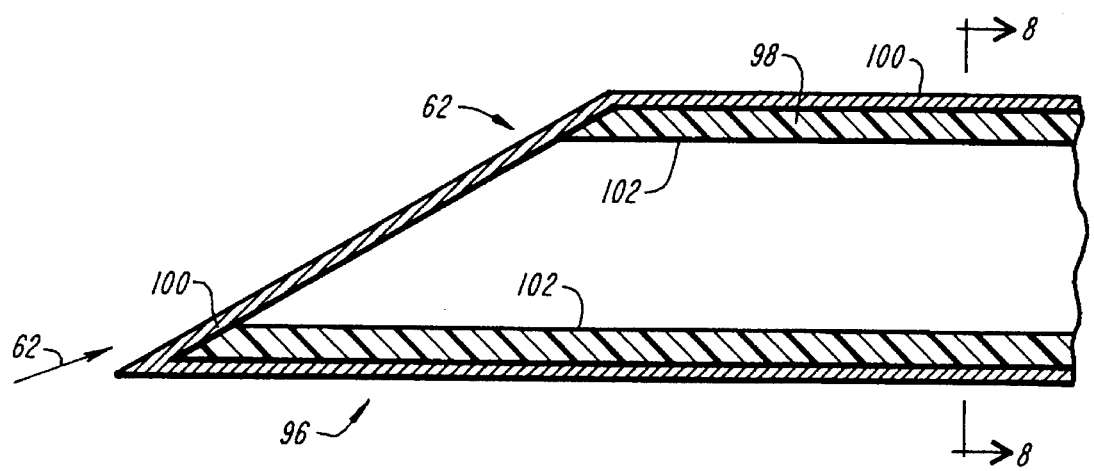
FIG. 7 is a longitudinal cross section, on an enlarged scale, of a polymeric catheter tip dry coated according to the invention.
Figure 8:
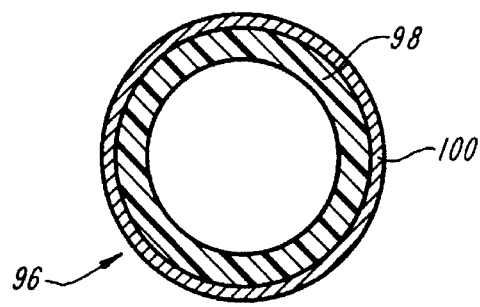
FIG. 8 is a section of the catheter tip shown in FIG. 7 in the direction of the arrows 8—8.

A polymeric catheter tip 96, dry-coated according to the invention and on an enlarged scale, is illustrated in section in FIGS. 7 and 8. The dry-coated polymeric catheter tip 96 comprises a polymeric catheter tip 98, coated on its outside surface as well as on its front beveled end with a bactericidal thin film 100. It will be observed that a small section on the inside front surface of the polymeric catheter tip 98 also is coated with a thin bactericidal film 102. It is to be pointed out that the thin bactericidal film 100 on the outside of the polymeric catheter tip 98 is of even thickness from about 0.5 microns to about ten (10) microns, whereas the thin bactericidal film 102 on the inside of the tip 98 is tapered and usually does not extend beyond the widest angle of the ion beam 62, as illustrated.

The thin bactericidal coatings 100 are not only of uniform thickness circumferentially and along the axial length of the catheter tip 98, the coatings also are characterized by being dense, free of pinholes, strongly adherent, hard yet flexible, clean and free of contaminants. Due to the ion beam assisted process, the desired thickness of the bactericidal coatings 100 is precisely controllable and adjustable, is reliable and reproducible. The dry-coating method, furthermore is environmentally safe, with no chemical residue being produced as a consequence of the process.

The Embodiments of FIGS. 9–12

In the embodiments of FIGS. 9–12, representative biomedical components made from a metallic material, such as stainless steel, and designed, at least in part, to enter the human body are illustrated.

Figure 9:
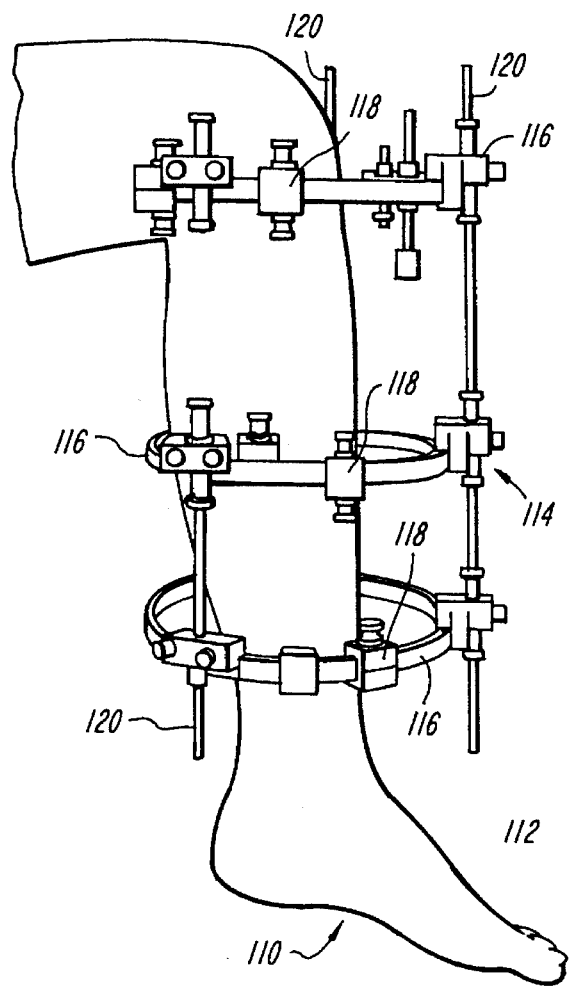
FIG. 9 is a picture of a limb below the knee to which an external fixation device, not provided with a bactericidal coating according to the invention, has been secured.

Specifically, FIG. 9 is a picture 110 of a limb 112 whose skeletal fracture has been stabilized by an external fixation device 114. The external fixation device 114, preferably formed of stainless steel, has not been provided with a coating of bactericidal compounds according to the invention so as to illustrate the consequences thereof. The external fixation device 114 essentially comprises a plurality of ¾ rings 116, each securing at least two transfixion pins 118 passing through the limb 112 and thereby stabilizing the affected internal skeletal fracture segments. It is primarily these pins 118 that cause the pin tract infections. The rings 116 are secured to one another by three threaded connecting rods 120.

Figure 10:
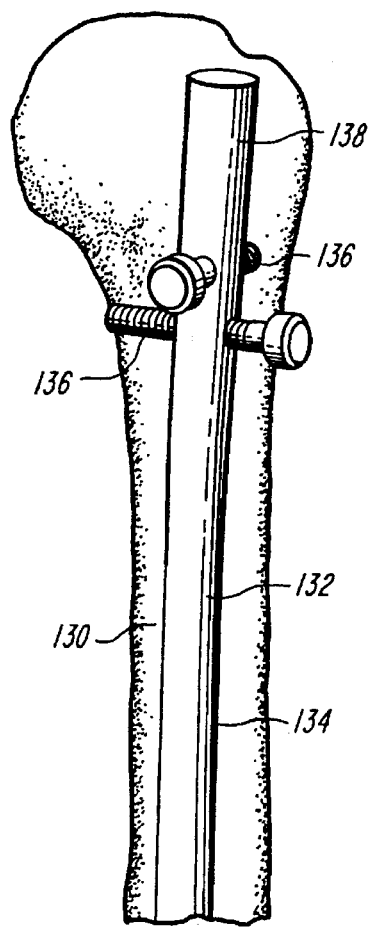
FIG. 10 is a fragmentary vertical section of a humerus with an intramedullary fixation nail, which has been provided with a bactericidal coating according to the invention, implanted therein.

FIG. 10 illustrates a humerus 130 in fragmentary vertical section, with an intramedullary fixation nail 132 implanted in its intramedullary canal 134 and secured therein by suitable screws 136. The intramedullary fixation nail 132 and its associated screws 136, preferably all formed of surgical stainless steel, have been provided with coatings 138 of bactericidal compounds in the form of ionized atoms thereof according to the invention. These thin coatings 138, not visible to the naked eye, are of an infection fighting compound as above described.

Figure 11:
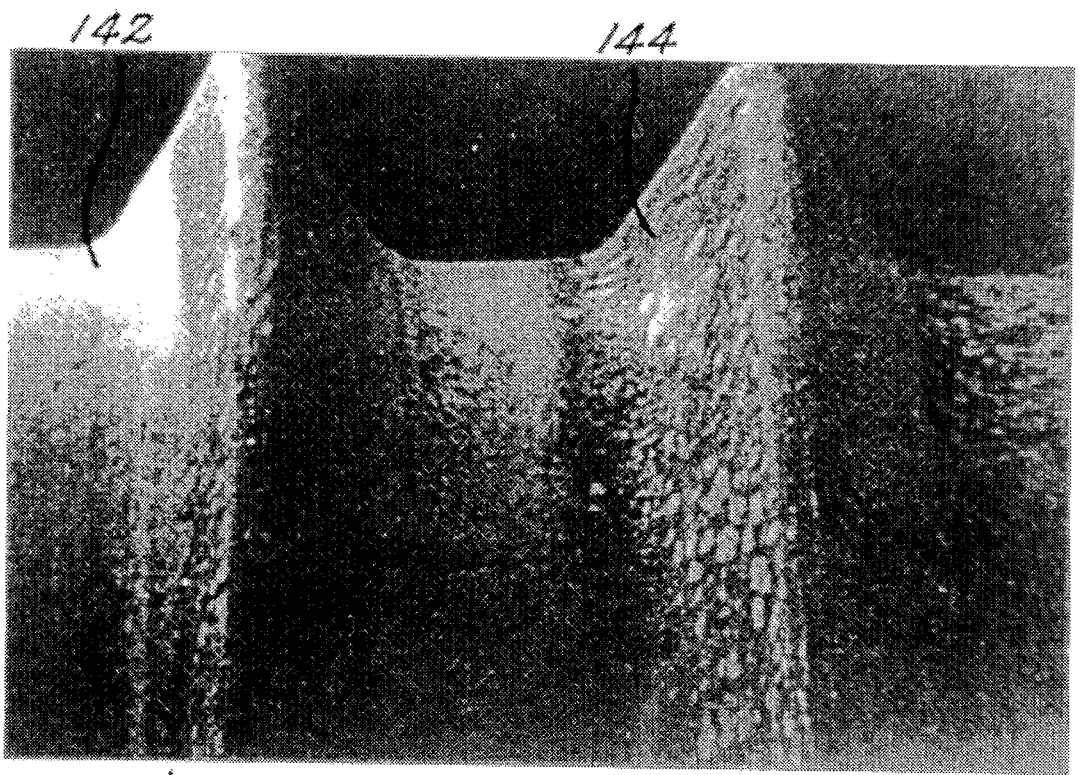
FIG. 11 is a picture of an external fixation pin, not provided with a bactericidal coating, on an enlarged scale, showing the signs of infection.
Figure 12:
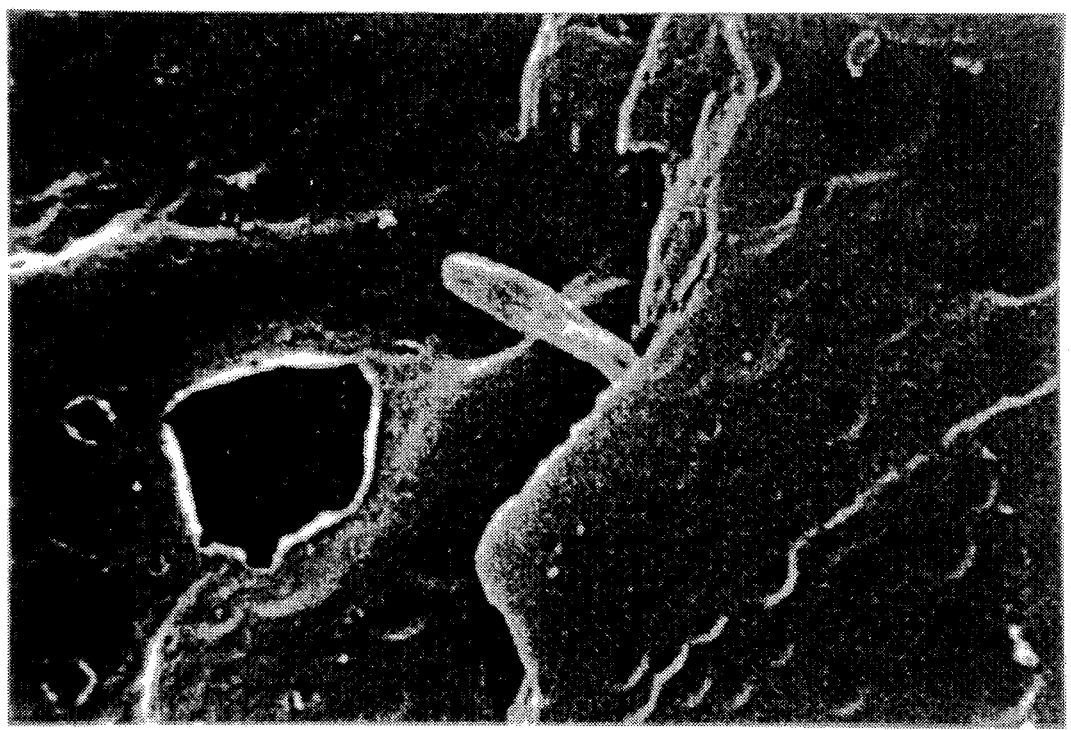
FIG. 12 is a picture of a part of the infected area, on an enlarged scale, on the external fixation pin of FIG. 11.

FIGS. 11 and 12 are reproductions of pictures taken from one of the above-mentioned articles, to wit, John Mahan, M.D., et al, "Factors in Pin Tract Infections," published in the March 1991 issue of *Orthopedics*, Vol. 14, No. 3, page 306.

FIG. 11 is a photograph 140 showing the surface of an external fixation pin 142, which like the transfixion pins 118 in FIG. 9, have not been provided with a bactericidal coating according to the invention, after removal from a patient, and illustrating visible signs of infection, as at 144. FIG. 12 is a photograph 150, on an enlarged scale, of a portion of the infected area on the pin 142 of FIG. 11.

Each of the metallic biomedical components illustrated in FIGS. 9–12, to wit, the external fixation device 114 and its components 116 and 118, as well as the intremedullary fixation nail 132 and its fixation screws 136, as well as the fixation pin 142 can all be dry-coated with the bactericidal coatings in an apparatus 30, as illustrated in FIG. 2 and provided with suitable fixtures 68 and 94 as illustrated in FIGS. 5 and 6, and adapted to hold and to present the implants to an ion beam 62, as above described.

As mentioned by John Mahan, M.D., et al in their said article, "The most significant complications in external fixation is pin tract infection (FIGS. 1–2). Rates ranging from 0.5% to 10% have been reported." Of the more than 200 pins removed from about 40 patients, they report that more than 40% of the pin tracts were inflamed and about three-quarters of the pin tips cultured positive for bacteria. "The predominant organism cultured was *Staphylococcus epidermidis* (90.6%), considered non-virulent, followed by virulent *Staphylococcus aureus* (37.5%), and *Escherichia coli* (9.4%)." It is the bacillus *Escherichia coli* that is illustrated in FIG. 12.

The illustrated biomedical components are merely representative of this class, which also includes metallic needles, metallic urological catheters, metallic percutaneous connectors and ceramic and metallic counterfaces in joint replacements, such as for the hip or the knee. Thus, all biomedical components, formed of polymer, metal or ceramic, designed to penetrate or enter into the body, are included herein. Most of the metallic biomedical components are formed of surgical stainless steel. Others are formed of titanium and cobalt-chromium. The bactericidal film 138 formed of a bactericidal compound can be readily applied in a reproducible, adherent manner to all known biomedical materials. The bactericidal compounds used to form the infection fighting film 138 according to the invention include: tungsten, titanium, platinum, iridium, gold, silver, mercury, copper, iodine, and their respective known alloys, compounds and oxides.

The process of the invention, as above described with reference to FIGS. 1 and 2, of providing biomedical components with the infection fighting film 138, preferably is carried out with the following operating parameters: a vacuum pressure of about $10^{-7}$ torrs, an ion beam current density from about 0.21 NA/cm$^2$ to about 5.67 NA/cm$^2$, with the substrate temperature ranging from about $-76°$ C. to about 200° C., an ion beam energy from about 200 eV to about 20 Kev, and with a deposition rate on the substrate ranging from about 10 Angstroms/second to about 1000 Angstroms per second.

EXAMPLE I

An external fixation device 114, in particular the transfixion pins 118 thereof, have been dry-coated in the apparatus 30 and in accord with the above-described process with the following operational parameters:

Evaporant: Ag
Deposition Rate: 5.0 nm/sec.
Ion Beam Energy: 5 keV
Current Density: 27.5 microamps/cm$^2$
Substrate Temperature: 15° C.
Ion Beam: O$^+$
Thickness of Bactericidal Film Being Deposited: 1.0 micron
Processing Time: 3 min., 20 sec.
Vacuum Pressure in Processing Chamber: $10^{-6}$ torr

EXAMPLE II

A metallic urological catheter has been dry-coated over its entire length in the apparatus 30 and in accord with the above-described process, employing the following operational parameters:

Evaporant: Ti
Deposition Rate: 7.5 nm/sec.
Ion Beam Energy: 5 keV
Current Density: 27.5 microamps/cm$^2$
Substrate Temperature: 25° C.
Ion Beam: Ar$^+$ and O$^+$
Thickness of Bactericidal Film Deposited: 0.5 micron
Processing Time: 1 min., 12 sec.
Vacuum Pressure in Processing Chamber: $10^{-6}$ torr

EXAMPLE III

A ceramic counterface has been dry-coated over its entire length in the apparatus 30 and in accord with the above-described process, employing the following operational parameters:

Evaporant: Au
Deposition Rate: 5.0 nm/sec.
Ion Beam Energy: 10 KeV
Current Density: 42.4 microamps/cm$^2$
Substrate Temperature: 20° C.
Ion Beam O$^+$ and Ar
Thickness of Bactericidal Film Deposited: 1.2 micron
Processing Time: 3 min., 50 secs.
Vacuum Pressure: $10^{-7}$ torr

EXAMPLE IV

A polymeric central venous stent has been dry-coated over its entire length in the apparatus 30 and in accord with the above-described process, employing the following operational parameters:

Evaporant: Ag
Deposition Rate: 7 nm/sec.
Ion Beam Energy: 10 keV
Current Density: 200 microamps/cm$^2$
Substrate Temperature: 10° C.
Ion Beam: Ar$^+$ and O$^+$
Thickness of Bactericidal Film Being Deposited: 1.0 micron
Processing Time: 2 min., 15 sec.
Vacuum Pressure in Processing Chamber: $10^{-7}$ torr Thus it has been shown and described polymeric, metallic and/or ceramic implants provided with bactericidal compounds which implants satisfy the objects and advantages set forth above.

Since certain changes may be made in the present disclosure without departing from the scope of the present invention, it is intended that all matter described in the accompanying drawings, be interpreted in an illustrative and not in a limiting sense.

What is claimed is:

1. A method for depositing a bactericidal coating on a polymeric biomedical implant by ion beam assisted deposition, comprising introducing a polymeric biomedical implant into an evacuated chamber, evaporating a bactericidal evaporant within the chamber to form a vapor of said evaporant proximate to said polymeric biomedical implant, introducing accelerated ions into the chamber, and bombarding at least a portion of said polymeric biomedical implant with the accelerated ions to drive said evaporant into said polymeric biomedical implant to form the bactericidal coating.

2. The method of claim 1 wherein the method further comprises continuing the evaporation and bombardment steps until the bactericidal coating has a thickness of at least about 0.01 microns.

3. The method of claim 1 wherein the method further comprises continuing the evaporation and bombardment steps until the bactericidal coating is formed having a thickness ranging between about 0.01 microns and about 10 microns.

4. The method of claim 1 wherein the step of bombarding the polymeric biomedical implant with the accelerated ions further comprises bombarding the polymeric biomedical implant with an ion beam having a beam energy of at least about 200 eV.

5. The method of claim 1 wherein the step of evaporating the bactericidal evaporant comprises evaporating a metallic evaporant.

6. The method of claim 5 wherein the metallic evaporant comprises at least one of silver, platinum, iridium, gold, mercury, copper and iodine.

7. The method of claim 5 wherein the step of bombarding the implant with accelerated ions comprises bombarding the implant with at least one of argon, oxygen, neon, and helium ions.

8. The method of claim 5 wherein the polymeric biomedical implant is one of a catheter, a stent, a faryngectomy flap, a tracheostomy tube, a hydrocephalic shunt and a percutaneous connector.

* * * * *

UNITED STATES PATENT AND TRADEMARK OFFICE
CERTIFICATE OF CORRECTION

PATENT NO. : 5,474,797
DATED : December 12, 1995
INVENTOR(S) : Piran Sioshansi et al.

It is certified that error appears in the above-indentified patent and that said Letters Patent is hereby corrected as shown below:

In column 3, line 59, please replace "$10^{-7}$ torr, with the temperature" with --$10^{-7}$ torr, an ion beam current density from about 0.21 to about 5.67 NA/cm$^2$, with the temperature--.

Signed and Sealed this

Eleventh Day of June, 1996

Attest:

BRUCE LEHMAN

*Attesting Officer*    Commissioner of Patents and Trademarks